United States Patent [19]

Newman et al.

[11] Patent Number: 5,436,163
[45] Date of Patent: Jul. 25, 1995

[54] POLYMORPHISM OF HUMAN PLATELET MEMBRANE GLYCOPROTEIN IIB AND DIAGNOSTIC APPLICATIONS THEREOF

[75] Inventors: Peter J. Newman, Shorewood; Richard H. Aster, Milwaukee, both of Wis.

[73] Assignee: The Blood Center of Southeastern Wisconsin, Wilwaukee, Wis.

[21] Appl. No.: 443,946

[22] Filed: Dec. 1, 1989

[51] Int. Cl.$^6$ .................... C12Q 1/68; C12P 19/34; C07H 21/04
[52] U.S. Cl. ..................... 435/6; 435/91.2; 536/24.31
[58] Field of Search ............ 435/6, 7, 91.2, 810; 436/63, 94, 501, 508, 808; 536/24.31, 24.33, 23.5

[56] References Cited

U.S. PATENT DOCUMENTS

| | | | |
|---|---|---|---|
| 4,582,788 | 4/1986 | Erlich et al. | 435/6 |
| 4,683,195 | 7/1987 | Mullis et al. | 435/6 |
| 4,699,880 | 10/1987 | Goldstein | 435/172.2 |
| 4,704,692 | 11/1987 | Lander | 364/496 |
| 4,752,582 | 6/1988 | Vanderlaan et al. | 435/240.27 |

(List continued on next page.)

FOREIGN PATENT DOCUMENTS 0200362 10/1986 European Pat. Off. .

OTHER PUBLICATIONS

Enzyme & Reagents for Molecular Biology, United States Biochemical Corp., p. 106, 1988, Cleveland, Ohio.

J. E. Sadler et al "The Role of Sialic Acid in the Expression of Human MN Blood Group Antigens" The Journal of Biological Chemistry, vol. 254, Mar., 1979, pp. 2112–2119.

H. Take et al, "Demonstration of the Heterogeneity of Epitopes etc." British Journal of Haematology, 1990, 76: pp. 395–400.

Lyman et al., *Blood* 75:No. 90275262 (Jun., 1990) (abstract).
Cong et al., *Hum. Genet.* 80:389–392 (1988) (abstract).
Bray et al., *Proc. Natl. Acad. Sci.* 85:8683–8687 (1988) (abstract).
Uzan et al., *Eur. J. Biochem.* 171:87–93 (1988) (abstract).
Bray et al., *J. Clin. Invest.* 80:1812–1817 (1987) (abstract).
Chomczynski et al., "Single-Step Method of RNA Isolation by Acid Guanidinium Thiocyanate-Phenol--Chloroform Extraction," *Anal. Biochem.* 162:156–159 (1987).
Furihata et al., "On the Association of the Platelet-Specific Alloantigen, Pen$^a$, with Glycoprotein IIIa," *J. Clin. Invest.* 80:1624 (1987).
Gillies et al., "Expression of Human Anti-Tetanus Toxoid Antibody in Transfected Murine Myeloma Cells," *Biotechnol.* 7:799–804 (1989).
Kickler et al., "Identification of Bak$^b$, a New Platelet-Specific Antigen Associated with Posttransfusion Purpura," *Blood* 71:894–898 (1988).

(List continued on next page.)

Primary Examiner—Margaret Parr
Assistant Examiner—Lisa Arthur
Attorney, Agent, or Firm—Foley & Lardner

[57] ABSTRACT

Isolated polynucleotide molecules and peptides encoded by these molecules can be used in the analysis of alloantigen phenotypes, as well as in diagnostic and therapeutic applications, relating to human platelet Bak polymorphism. By analyzing genomic DNA or amplified genomic DNA, or amplified cDNA derived from platelet mRNA, it is possible to type glycoprotein GPIIb with regard to the Bak polymorphism, for example, in the context of diagnosing and treating clinical syndromes associated with GPIIb-related immune responses.

17 Claims, 15 Drawing Sheets

U.S. PATENT DOCUMENTS

| | | | |
|---|---|---|---|
| 4,800,159 | 1/1989 | Mullis et al. | 435/172.3 |
| 4,810,632 | 3/1989 | McMillan | 435/91.2 |
| 4,935,357 | 6/1990 | Szybalski | 435/91.2 |

OTHER PUBLICATIONS

Kiefel et al., "Posttransfusion Purpura Associated with an Anti-Bak$^b$", Vox Sang. 56:93–97 (1989).

Landegren et al., "A Ligase-Mediated Gene Detection Technique," *Science* 241:1077–1080 (1988).

Maniatis et al., "Molecular Cloning: A Lab Manual", pp. 187–210 (Cold Spring Harbour Laboratory, 1982).

Nakatani et al., "Functional Expression of Human Monoclonal Antibody Genes Directed Against Pseudomonal Exotoxin A In Mouse Myeloma Cells," *Biotechnol.* 7:805–810 (1989).

Newman et al., "Enzymatic Amplification of Platelet-Specific Messenger RNA Using the Polymerase Chain Reaction," *J. Clin. Invest.* 82:739–743 (1988).

Newman et al., "The Human Platelet Alloantigens, PI$^{A1}$ and PI$^{A2}$, Are Associated with a Leucine$^{33}$/Proline$^{33}$ Amino Acid Polymorphism in Membrane Glycoprotein IIIa, and Are Distinguishable by DNA Typing," *J. Clin. Invest.* 83:1778–1771 (1989).

Phillips et al., "The Platelet Membrane Glycoprotein IIb–IIIa Complex," *Blood* 71:831–843 (1988).

Poncz et al., "Structure of the Platelet Membrane Glycoprotein IIb," *J. Biol. Chem.,* 262:8476 (1987).

von dem Borne et al., "Bak$^a$, a New Platelet-Specific Antigen Involved in Neonatal Allo-Immune Thrombocytopenia," *Vox. Sang.* 38:113–120 (1980).

AMPLIFICATION OF THE C-TERMINAL REGION OF PLATELET MEMBRANE GPIIb

AMINO ACID SEQUENCE POLYMORPHISM ASSOCIATED WITH THE Bak$^a$/Bak$^b$ HUMAN PLATELET ALLOANTIGEN SYSTEM

| GPIIb HEAVY CHAIN | GPIIb LIGHT CHAIN |
|---|---|
| ....VDWGLPIPSPSPIHPAHHKRDRR | QIFLPEPEQPSRL.... |
| ....VDWGLPSPSPSPIHPAHHKRDRR | QIFLPEPEQPSRL.... |

Bak / PMI-1

DOT BLOT OLIGONUCLEOTIDE HYBRIDIZATION ANALYSIS OF Bak PHENOTYPE

FIG. 5A

```
           10         20          30          40          50
           -          -           -           -           -
GATG GCC AGA GCT TTG TGT CCA CTG CAA GCC CTC TGG CTT CTG GAG TGG GTG CTG
 Met Ala Arg Ala Leu Cys Pro Leu Gln Ala Leu Trp Leu Leu Glu Trp Val Leu 60          70          80          90          100
     -           -           -           -           -
CTG CTC TTG CCT TGT GCT GCC CCT CCA GCC TGG GCC TTG AAC CTG GAC CCA
Leu Leu Leu Gly Pro Cys Ala Ala Pro Pro Ala Trp Ala Leu Asn Leu Asp Pro 110         120         130         140         150         160
-           -           -           -           -           -
GTG CAG CTC ACC TTC TAT GCA GGC CCC AAT GGC AGC CAG TTT GGA TTT TCA CTG
 Val Gln Leu Thr Phe Tyr Ala Gly Pro Asn Gly Ser Gln Phe Gly Phe Ser Leu 170         180         190         200         210
     -           -           -           -           -
GAC TTC CAC AAG GAC AGC CAT GGG AGA GTG GCC ATC GTG GGC GCC CCG CGG
 Asp Phe His Lys Asp Ser His Gly Arg Val Ala Ile Val Gly Ala Pro Arg 220         230         240         250         260         270
-           -           -           -           -           -
ACC CTG GGC CCC AGC CAG GAG GAG ACG GGC GGC GTG TTC CTG TGC CCC TGG AGG
 Thr Leu Gly Pro Ser Gln Glu Glu Thr Gly Gly Val Phe Leu Cys Pro Trp Arg
```

FIG. 5B

```
      280         290         300         310         320
       |           |           |           |           |
GCC GAG GGC GGC CAG TGC CCC TCG CTG CTC TTT GAC CTC CGT GAT GAG ACC CGA
Ala Glu Gly Gly Gln Cys Pro Ser Leu Leu Phe Asp Leu Arg Asp Glu Thr Arg 330         340         350         360         370
       |           |           |           |           |
AAT GTA GGC TCC CAA ACT TTA CAA ACC TTC AAG GCC CGC CAA GGA CTG GGG GCG
Asn Val Gly Ser Gln Thr Leu Gln Thr Phe Lys Ala Arg Gln Gly Leu Gly Ala 380         390         400         410         420         430
       |           |           |           |           |           |
TCG GTC GTC AGC TGG AGC GAC GTC ATT GTG GCC TGC GCC CCC TGG CAG CAC TGG
Ser Val Val Ser Trp Ser Asp Val Ile Val Ala Cys Ala Pro Trp Gln His Trp 440         450         460         470         480
       |           |           |           |           |
AAC GTC CTA GAA AAG ACT GAG GCT GAG AAG ACG CCC GTA GGT AGC TGC TTT
Asn Val Leu Glu Lys Thr Glu Ala Glu Lys Thr Pro Val Gly Ser Cys Phe 490         500         510         520         530         540
       |           |           |           |           |           |
TTG GCT CAG CCA GAG AGC GGC CGC GCC GAG TAC TCC CCC TGT CGC GGG AAC
Leu Ala Gln Pro Glu Ser Gly Arg Arg Ala Glu Tyr Ser Pro Cys Arg Gly Asn
```

FIG. 5C

```
550
ACC CTG AGC CGC ATT TAC GTG GAA AAT GAT TTT AGC TGG GAC AAG CGT TAC TGT
Thr Leu Ser Arg Ile Tyr Val Glu Asn Asp Phe Ser Trp Asp Lys Arg Tyr Cys

600
GAA GCG GGC TTC AGC TCC GTG GTC ACT CAG GCC GGA GAG CTG GTG CTT GGG GCT
Glu Ala Gly Phe Ser Ser Val Val Thr Gln Ala Gly Glu Leu Val Leu Gly Ala

650
CCT GGC GGC TAT TAT TTC TTA GGT CTC CTG GCC CAG GCT CCA GTT GCG GAT ATT
Pro Gly Gly Tyr Tyr Phe Leu Gly Leu Leu Ala Gln Ala Pro Val Ala Asp Ile

700
TTC TCG AGT TAC CGC CCA GGC ATC CTT TTG TGG CAC GTG TCC TCC CAG AGC CTC
Phe Ser Ser Tyr Arg Pro Gly Ile Leu Leu Trp His Val Ser Ser Gln Ser Leu

750
TCC TTT GAC TCC AGC AAC CCA GAG TAC TTC GAC GGC TAC TGG GGG TAC TCG GTG
Ser Phe Asp Ser Ser Asn Pro Glu Tyr Phe Asp Gly Tyr Trp Gly Tyr Ser Val
```

FIG. 5D

```
       820         830         840         850         860
        |           |           |           |           |
GCC GTG GGC GAG TTC GAC GGG GAT CTC AAC ACT ACA GAA TAT GTC GTC GGT GCC
Ala Val Gly Glu Phe Asp Gly Asp Leu Asn Thr Thr Glu Tyr Val Val Gly Ala 870         880         890         900         910
        |           |           |           |           |
CCC ACT TGG AGC CTG GGA GCG GTG GAA ATT TTG GAT TCC TAC TAC CAG
Pro Thr Trp Ser Leu Gly Ala Val Glu Ile Leu Asp Ser Tyr Tyr Gln 920         930         940         950         960         970
  |           |           |           |           |           |
AGG CTG CAT CGG CTG CGC GGA GAG CAG ATG GCG TCG TAT TTT GGG CAT TCA GTG
Arg Leu His Arg Leu Arg Gly Glu Gln MET Ala Ser Tyr Phe Gly His Ser Val 980         990         1000        1010        1020
        |           |           |           |           |
GCT GTC ACT GAC GTC AAC GGG GAT GGG AGG CAT GAT CTG CTG GTG GGC GCT CCA
Ala Val Thr Asp Val Asn Gly Asp Gly Arg His Asp Leu Leu Val Gly Ala Pro 1030        1040        1050        1060        1070        1080
  |           |           |           |           |           |
CTG TAT ATG GAG AGC CGG GCA GAC CGA AAA CTG GCC GAA GTG GGG CGT GTG TAT
Leu Tyr MET Glu Ser Arg Ala Asp Arg Lys Leu Ala Glu Val Gly Arg Val Tyr
```

FIG. 5E

```
          1090       1100       1110       1120       1130
           |          |          |          |          |
TTG TTC CTG CAG CCG CGA GGC CCC CAC GCG CTG GGT GCC CCC AGC CTC CTG CTG
Leu Phe Leu Gln Pro Arg Gly Pro His Ala Leu Gly Ala Pro Ser Leu Leu Leu 1140       1150       1160       1170       1180
           |          |          |          |          |
ACT GGC ACA CAG CTC TAT GGG CGA TTC GGC TCT GCC ATC GCA CCC CTG GGC GAC
Thr Gly Thr Gln Leu Tyr Gly Arg Phe Gly Ser Ala Ile Ala Pro Leu Gly Asp 1190       1200       1210       1220       1230       1240
           |          |          |          |          |          |
CTC GAC CGG GAT GGC TAC AAT GAC ATT GCA GTG GCT GCC TAC GGG GGT CCC
Leu Asp Arg Asp Gly Tyr Asn Asp Ile Ala Val Ala Ala Pro Tyr Gly Gly Pro 1250       1260       1270       1280       1290
           |          |          |          |          |
AGT GGC CGG GGC CAA GTG CTG GTG TTC CTG GGT CAG AGT GAG GGG CTG AGG TCA
Ser Gly Arg Gly Gln Val Leu Val Phe Leu Gly Gln Ser Glu Gly Leu Arg Ser 1300       1310       1320       1330       1340       1350
           |          |          |          |          |          |
CGT CCC TCC CAG GTC CTG GAC AGC CCC TTC CCC ACA GGC TCT GCC TTT GGC TTC
Arg Pro Ser Gln Val Leu Asp Ser Pro Phe Pro Thr Gly Ser Ala Phe Gly Phe
```

FIG. 5F

```
       1360          1370          1380          1390          1400
        ---           ---           ---           ---           ---
TCC CTT CGA GGT GCC GTA GAC ATC GAT GAC AAC GGA TAC CCA GAC CTG ATC GTG
Ser Leu Arg Gly Ala Val Asp Ile Asp Asp Asn Gly Tyr Pro Asp Leu Ile Val 1410          1420          1430          1440          1450
        ---           ---           ---           ---           ---
GGA GCT TAC GGG GCC AAC CAG GTG GCT GTG TAC AGA GCT CAG CCA GTG GTG AAG
Gly Ala Tyr Gly Ala Asn Gln Val Ala Val Tyr Arg Ala Gln Pro Val Val Lys 1460         1470          1480          1490          1500          1510
  ---          ---           ---           ---           ---           ---
GCC TCT GTC CAG CTA CTG GTG CAA GAT TCA CTG AAT CCT GCT GTG AAG AGC TGT
Ala Ser Val Gln Leu Leu Val Gln Asp Ser Leu Asn Pro Ala Val Lys Ser Cys 1520          1530          1540          1550          1560
        ---           ---           ---           ---           ---
GTC CTA CCT CAG ACC AAG ACA CCC GTG AGC TGC TTC AAC ATC CAG ATG TGT GTT
Val Leu Pro Gln Thr Lys Thr Pro Val Ser Cys Phe Asn Ile Gln MET Cys Val 1570         1580          1590          1600          1610          1620
  ---          ---           ---           ---           ---           ---
GGA GCC ACT GGG CAC AAC ATT CCT CAG AAG CTA TCC CTA AAT GCC GAG CTG CAG
Gly Ala Thr Gly His Asn Ile Pro Gln Lys Leu Ser Leu Asn Ala Glu Leu Gln
```

FIG. 5G

1630 CTG GAC CGG CAG AAG CCC CGC CAG GGC CGG GTG CTG CTG GGC TCT CAA 1670
Leu Asp Arg Gln Lys Pro Arg Gln Gly Arg Arg Val Leu Leu Gly Ser Gln

1680 CAG GCA GGC ACC ACC CTG AAC CTG GAT CTG GGC GGA AAG CAC AGC CCC ATC TGC 1720
Gln Ala Gly Thr Thr Leu Asn Leu Asp Leu Gly Gly Lys His Ser Pro Ile Cys

1730 CAC ACC ATG GCC TTC CTT CGA GAT GAG GCA GAC TTC CGG GAC AAG CTG AGC 1780
His Thr MET Ala Phe Leu Arg Asp Glu Ala Asp Phe Arg Asp Lys Leu Ser

1790 CCC ATT GTG CTC AGC CTC AAT GTG TCC CTA CCG CCC ACG GAG GCT GGA ATG GCC 1830
Pro Ile Val Leu Ser Leu Asn Val Ser Leu Pro Pro Thr Glu Ala Gly MET Ala

1840 CCT GCT GTC CTG CAT GGA GAC ACC CAT GTG CAG GAG CAG ACA CGA ATC GTC 1890
Pro Ala Val Leu His Gly Asp Thr His Val Gln Glu Gln Thr Arg Ile Val

FIG. 5H

```
        1900        1910        1920        1930        1940
         ---         ---         ---         ---         ---
CTG GAC TGT GGG GAA GAT GAC GTA TGT GTG CCC CAG CTT CAG CTC ACT GCC AGC
Leu Asp Cys Gly Glu Asp Asp Val Cys Val Pro Gln Leu Gln Leu Thr Ala Ser 1950        1960        1970        1980        1990
         ---         ---         ---         ---         ---
GTG ACG GGC TCC CCG CTC CTA GTT GGG GCA GAT AAT GTC CTG GAG CTG CAG ATG
Val Thr Gly Ser Pro Leu Leu Val Gly Ala Asp Asn Val Leu Glu Leu Gln MET 2000        2010        2020        2030        2040        2050
 ---         ---         ---         ---         ---         ---
GAC GCA GCC AAC GAG GGC GAG GGG GCC TAT GAA GCA GAG CTG GCC GTG CAC CTG
Asp Ala Ala Asn Glu Gly Glu Gly Ala Tyr Glu Ala Glu Leu Ala Val His Leu 2060        2070        2080        2090        2100
         ---         ---         ---         ---         ---
CCC CAG GGC GCC CAC TAC ATG CGG GCC CTA AGC AAT GTC GAG GGC TTT GAG AGA
Pro Gln Gly Ala His Tyr MET Arg Ala Leu Ser Asn Val Glu Gly Phe Glu Arg 2110        2120        2130        2140        2150        2160
 ---         ---         ---         ---         ---         ---
CTC ATC TGT AAT CAG AAG AAG GAG AAT GAG ACC AGG GTG GTG CTG TGT GAG CTG
Leu Ile Cys Asn Gln Lys Lys Glu Asn Glu Thr Arg Val Val Leu Cys Glu Leu
```

FIG. 5I

```
        2170        2180        2190        2200        2210
         |           |           |           |           |
GGC AAC CCC ATG AAG AAG AAC GCC CAG ATA GGA ATC GCG ATG TTG GTG AGC GTG
Gly Asn Pro MET Lys Lys Asn Ala Gln Ile Gly Ile Ala MET Leu Val Ser Val 2220        2230        2240        2250        2260
         |           |           |           |           |
GGG AAT CTG GAA GAG GCT GGG GAG TCT GTG TCC TTC CAG CTG CAG ATA CGG AGC
Gly Asn Leu Glu Glu Ala Gly Glu Ser Val Ser Phe Gln Leu Gln Ile Arg Ser 2270        2280        2290        2300        2310        2320
         |           |           |           |           |           |
AAG AAC AGC CAG AAT CCA AAC AGC AAG ATT GTG CTG CTG GAC GTG CCG GTC CGG
Lys Asn Ser Gln Asn Pro Asn Ser Lys Ile Val Leu Leu Asp Val Pro Val Arg 2330        2340        2350        2360        2370
         |           |           |           |           |
GCA GAG GCC CAA GTG GAG GAG CTG CGA GGG AAC TCC TTT CCA GCC TCC CTG GTG
Ala Glu Ala Gln Val Glu Glu Leu Arg Gly Asn Ser Phe Pro Ala Ser Leu Val Val 2380        2390        2400        2410        2420        2430
         |           |           |           |           |           |
GCA GCA GAA GAA GGT GAG AGG GAG CAG AAC AGC TTG GAC AGC TGG GGA CCC AAA
Ala Ala Glu Glu Gly Glu Arg Glu Gln Asn Ser Leu Asp Ser Trp Gly Pro Lys
```

FIG. 5J

```
     2440         2450         2460         2470         2480
      ---          ---          ---          ---          ---
GTG GAG CAC ACC TAT GAG CTC CAC AAC AAT GGC CCT GGG ACT GTG AAT GGT CTT
Val Glu His Thr Tyr Glu Leu His Asn Asn Gly Pro Gly Thr Val Asn Gly Leu 2490         2500         2510         2520         2530
      ---          ---          ---          ---          ---
CAC CTC AGC ATC CAC CTT CCG GGA CAG TCC CAG CCC TCC GAC CTG CTC TAC ATC
His Leu Ser Ile His Leu Pro Gly Gln Ser Gln Pro Ser Asp Leu Leu Tyr Ile 2540         2550         2560         2570         2580         2590
 ---          ---          ---          ---          ---          ---
CTG GAT ATA CAG CCC CAG GGG GGC CTT CAG TGC TTC CCA CAG CCT CCT GTC AAC
Leu Asp Ile Gln Pro Gln Gly Gly Leu Gln Cys Phe Pro Gln Pro Pro Val Asn 2600         2610         2620         2630         2640
      ---          ---          ---          ---          ---
CCT CTC AAG GTG GAC TGG GGG CTG CCC ATC CCC AGC CCC TCC CCC ATT CAC CCG
Pro Leu Lys Val Asp Trp Gly Leu Pro Ile Pro Ser Pro Ser Pro Ile His Pro 2650         2660         2670         2680         2690         2700
 ---          ---          ---          ---          ---          ---
GCC CAT CAC AAG CGG GAT CGC AGA CAG ATC TTC CTG CCA GAG CCC GAG CAG CCC
Ala His His Lys Arg Asp Arg Arg Gln Ile Phe Leu Pro Glu Pro Glu Gln Pro
```

FIG. 5K

```
2710        2720        2730        2740        2750
 |           |           |           |           |
TCG AGG CTT CAG GAT CCA GTT CTC GTA AGC TGC GAC TCG GCG CCC TGT ACT GTG
Ser Arg Leu Gln Asp Pro Val Leu Val Ser Cys Asp Ser Ala Pro Cys Thr Val 2760        2770        2780        2790        2800
 |           |           |           |           |
GTG CAG TGT GAC CTG CAG GAG ATG GCG CGC GGG CAG CGG GCC ATG GTC ACG GTG
Val Gln Cys Asp Leu Gln Glu MET Ala Arg Gly Gln Arg Ala MET Val Thr Val 2810        2820        2830        2840        2850        2860
 |           |           |           |           |           |
CTG GCC TTC CTG TGG CTG CCC AGC CTC TAC CAG AGG CCT CTG GAT CAG TTT GTG
Leu Ala Phe Leu Trp Leu Pro Ser Leu Tyr Gln Arg Pro Leu Asp Gln Phe Val 2870        2880        2890        2900        2910
 |           |           |           |           |
CTG CAG TCG CAC GCA TGG TTC AAC GTG TCC CTC CCC TAT GCG GTG CCC CCG
Leu Gln Ser His Ala Trp Phe Asn Val Ser Ser Leu Pro Tyr Ala Val Pro Pro 2920        2930        2940        2950        2960        2970
 |           |           |           |           |           |
CTC AGC CTG CCC CGA GGG GAA GCT CAG GTG TGG ACA CAG CTC CGG GCC TTG
Leu Ser Leu Pro Arg Gly Glu Ala Gln Val Trp Thr Gln Leu Leu Arg Ala Leu
```

FIG. 5L

```
        2980        2990        3000        3010        3020
         |---        |---        |---        |---        |---
        GAG GAG AGG GCC ATT CCA ATC TGG TGG GTG CTG GTG GGT GTG CTG GGT GGC CTG
        Glu Glu Arg Ala Ile Pro Ile Trp Trp Val Leu Val Gly Val Leu Gly Gly Leu 3030        3040        3050        3060        3070
         |---        |---        |---        |---        |---
        CTG CTC ACC ATC CTG GTC CTG GCC ATG TGG AAG GTC GGC TTC TTC AAG CGG
        Leu Leu Thr Ile Leu Val Leu Ala MET Trp Lys Val Gly Phe Phe Lys Arg 3080        3090        3100        3110        3120        3130
 |---        |---        |---        |---        |---        |---
AAC CGG CCA CCC CTG GAA GAT GAT GAA GAG GGG GAG TGA TGG TGC AGC CTA
Asn Arg Pro Pro Leu Glu Asp Asp Glu Glu Gly Glu TER 3140        3150        3160        3170        3180
         |---        |---        |---        |---        |---
        CAC TAT TCT AGC AGG AGG GTT GGG CGT GCT ACC TGC ACC GCC CCT TCT CCA ACA 3190        3200        3210        3220        3230        3240
 |---        |---        |---        |---        |---        |---
AGT TGC CTC CAA GCT TTG GGT TGG AGC TGT TCC ATT GGG TCC TCT TGG TGT CGT
```

FIG. 5M

```
      3250         3260         3270         3280         3290
       --           --           --           --           --
TTC CCT CCC AAC AGA GCT GGG CTA CCC CCC CTC CTG CTG CCT AAT AAA GAG ACT 3300         3310
       --           --
GAG CCC TGA AAA AAA A
```

POLYMORPHISM OF HUMAN PLATELET MEMBRANE GLYCOPROTEIN IIB AND DIAGNOSTIC APPLICATIONS THEREOF

This invention was made with Government support under grant R29 HL38166-02, "Biochemical Studies of Human Platelet Alloantigens," and grant R37-HL-13629, "Hemorrhagic Diseases," awarded by the National Institutes of Health. The Government has certain rights in the invention.

BACKGROUND OF THE INVENTION

The present invention relates to isolated polynucleotide molecules useful for analyzing alloantigen phenotypes, to peptides encoded by these molecules, and to the diagnostic and therapeutic uses thereof relating to a human platelet Bak polymorphism, including a method for typing platelet membrane glycoproteins which entails an analysis of amplified cDNA produced from platelet mRNA or of genomic DNA.

Blood obtained from different individuals has been found to have different antigenic and immune properties, to the extent that antibodies in the blood of one person may react with antigens on red blood cells or platelets in the blood of another individual. These antigens are often found on membrane glycoproteins present on the surface of the cells. These membrane glycoprotein antigens can induce the production of antibodies against them when they are introduced as foreign proteins in transfused blood or in fetal blood. Human platelets and red blood cells contain dozens of identifiable membrane glycoprotein constituents, only some of which have been well characterized.

Membrane glycoproteins which induce antibody production in the same species are called "alloantigens." Alloantigens have been characterized for both red blood cells and platelets. Recognized classes of red blood cell and platelet alloantigens have been described, over the past 30 years, based on observations of antibody reactions occurring when patients have been exposed to blood from other individuals. The lack of sequenceable antigen protein and clonable antigen-encoding mRNA has prevented molecular characterization of the different alleles coding for many clinically important alloantigens.

One system of alloantigens, consisting of the platelet Bak$^a$ and Bak$^b$ alloantigens, are carried by the human platelet membrane glycoprotein IIb-IIIa (GPIIb-GPIIIa) complex, which mediates platelet aggregation by providing functional receptors for fibrinogen on platelet surfaces. See Phillips, et al., Blood 71:831-43 (1988). GPIIb and GPIIIa are known to bear a number of clinically important, alloantigenic determinants which are responsible for eliciting an immune response in two well-described clinical syndromes, post-transfusion purpura (PTP) and neonatal alloimmune thrombocytopenia (NATP). See Kunicki & Newman in CURRENT STUDIES IN HEMATOLOGY AND BLOOD TRANSFUSION 18-32 (1986); Aster in ADVANCES IN IMMUNOLOGY AND BONE MARROW TRANSPLANTATION 103-118 (1984).

The Bak alloantigen system is the second or third most frequently implicated stimulus in these disorders. There are two serologically defined, but molecularly undefined, allelic forms of the Bak alloantigen, designated "Bak$^a$" and "Bak$^b$," which are thought to be expression products of the GPIIb gene. von dem Borne, et al., Vox Sang. 39:113 (1980); Kickler, et al., Blood: 71(4):894 (1988); Keifel, et al., Vox Sang. 56:93 (1989). The gene frequencies for these two alleles have been calculated to be 61% for Bak$^a$ and 39% for Bak$^b$ while the observed phenotypic frequencies are 37% for Bak$^a$ homozygous, 15% for Bak$^b$ homozygous, and 48% for heterozygous individuals. see Kickler, et al., Vox Sang. 56:93 (1989). Based upon these frequencies, the probability of fetal-maternal Bak incompatibility would be significant, but fewer than 5% of the cases of NATP (or 1/40,000) are attributable to Bak. This suggests that other factors contribute to the likelihood of developing NATP.

Determination of the amino acid sequence variations that are presumably responsible for forming the relevant epitopes of red blood cell and platelet alloantigens has been achieved in only a few instances, due largely to the formidable difficulties in obtaining protein-sequence information from those often large glycoproteins. In particular, the amino acid-sequence variation responsible for the relevant epitopes has not yet been reported for either the Bak$^a$ or Bak$^b$ forms of the 125 kilodalton (kd) GPIIb molecule.

SUMMARY OF THE INVENTION

It is therefore an object of the present invention to provide polynucleotide molecules that can be used in analyzing Bak alloantigen.

It is also an object of the present invention to provide for the typing of human platelets, based on information obtained through the analysis of nucleic acids, including genomic DNA and cDNA derived from platelets, respectively.

It is yet another object of the present invention to provide ready means for determining platelet Bak alloantigen phenotype.

It is still a further object of the present invention to provide polypeptide molecules for use in generating antibodies that distinguish between the different forms of GPIIb which constitute the Bak polymorphism.

Another object of the present invention is to provide methods for diagnosing and treating clinical syndromes related to a GPIIb-related immune response.

In achieving these objects, there has been provided, in accordance with one aspect of the present invention, an oligonucleotide probe molecule that hybridizes to a portion of the GPIIb gene, which portion includes a nucleotide corresponding to nucleotide 2622 of GPIIb cDNA, where the molecule hybridizes to the portion in question when nucleotide 2622 is guanylate, for one type of allele-specifc probe, or thymidylate for another type. In a preferred embodiment, the oligonucleotide probe of the present invention is is between about ten and thirty bases in length.

In accordance with another aspect of the present invention, a kit for typing platelet Bak alloantigens has been provided that comprises (a) a receptacle containing a solution of a labeled oligonucleotide probe that distinguishes an allele of a platelet Bak alloantigen from other alleles, or (b) a receptacle containing a solution of an antibody that discriminately binds a Bak$^a$ allele or a Bak$^b$ allele of GPIIb, where the antibody (i) recognizes a polypeptide molecule encoded by a nucleotide sequence encoding at least amino acid 843 of GPIIb and (ii) binds either the Bak$^a$ allele or the Bak$^b$ allele of GPIIb, or (c) a receptacle containing a solution of an endonuclease recognizing a cleavage site that distinguishes a nucleotide sequence of an allele of a platelet Bak alloantigen from other alleles, and (d) means for amplifying DNA that comprises at least a portion of a GPIIb gene or GPIIb cDNA, where the portion in question includes a nucleotide corresponding to nucleotide 2622 of GPIIb cDNA.

There has also been provided, in accordance with another aspect of the present invention, a method of typing glycoprotein IIb, comprising the steps of (A) synthesizing cDNA from human platelet mRNA of an individual; (B) amplifying the cDNA to produce amplified cDNA; and then (C) analyzing the amplified cDNA to determine Bak alloantigen phenotype for that individual. In one preferred embodiment, the further comprises synthesizing cDNA from human platelet mRNA of a second individual, repeating aforementioned steps (B) and (C) on the cDNA of second individual, and thereafter discriminating between the first and second individuals based on the alloantigen phenotype. In another preferred embodiment, step (C) comprises the steps of (i) digesting the amplified cDNA with a restriction endonuclease recognizing a cleavage site that distinguishes a nucleotide sequence of a first Bak allele from another Bak allele; and then (ii) analyzing the cDNA fragments to determine the Bak alloantigen phenotype.

In accordance with yet another aspect of the present invention, a method of typing platelet Bak membrane glycoproteins has been provided that comprises the steps of (A) obtaining genomic DNA from an individual and (B) analyzing the genomic DNA to determine a platelet Bak alloantigen phenotype. In a preferred embodiment, step (B) comprises (i) digesting the genomic DNA with a restriction endonuclease to produce DNA fragments; thereafter (ii) hybridizing the DNA fragments with a labeled, allele-specific oligonucleotide probe that distinguishes a nucleotide sequence of an allele of a platelet Bak alloantigen from other alleles; and then (iii) analyzing the probe that has hybridized to the DNA fragments in order to determine the Bak alloantigen phenotype.

In accordance with still another aspect of the present invention, there has been provided a method of typing platelets with respect to GPIIb that comprises the steps of (A) obtaining genomic DNA from an individual, (B) amplifying the genomic DNA to produce amplified genomic DNA and (C) analyzing the amplified genomic DNA to determine a platelet Bak alloantigen phenotype. In a preferred embodiment, step (C) comprises of (i) hybridizing the amplified genomic DNA with a labeled, allele-specific oligonucleotide probe that distinguishes a nucleotide sequence of a first Bak allele from that of another Bak allele; and then (ii) analyzing the probe that has hybridized to the amplified genomic DNA to determine said alloantigen phenotype. In another preferred embodiment, step (C) comprises (i) hybridizing the amplified genomic DNA with a pair of oligonucleotide probes to form a construct, wherein a first probe of the pair of probes is labeled with a first label and the other probe is labeled with a second label, such that the first label is distinguishable from the second label, and the probes hybridize adjacently to each other at a nucleotide that distinguishes a Bak allele from another Bak allele; thereafter (ii) reacting said construct with a ligase in a reaction medium; and then (iii) analyzing said reaction medium to detect the presence of a ligation product comprising the first probe the said second probe.

A polypeptide molecule is further provided, in accordance with another aspect of the present invention, that comprises an amino-acid sequence that corresponds to a tetramer fragment of GPIIb, wherein the fragment comprises amino acid 843 of GPIIb and wherein the molecule is not GPIIb itself. Preferably, the polypeptide molecule is between four and fifty amino-acid residues in length. In addition, it is preferred that the polypeptide molecule is itself immunogenic or is attached to a immunogenicity-imparting carrier, forming another molecule of the present invention.

According to another aspect of the present invention, an antibody is provided that distinguishes the $Bak^a$ form of GPIIB antigen from the $Bak^b$ form, where the antibody recognizes a polypeptide sequence that comprises at least amino acid 843 of GPIIb. The antibody can be a monoclonal antibody produced by a method comprising the steps of (A) immunizing a mammal with an antigenic molecule comprising a polypeptide as described above, then (B) removing lymphocytes from the mammal, (C) fusing the lymphocytes with mammalian myeloma cells to form hybridoma cells, (D) culturing the hybridoma cells and thereafter (E) selecting, isolating and cloning hybridoma cells secreting monoclonal antibodies that distinguish between the $Bak^a$ and $Bak^b$ forms of GPIIb.

A method is also provided, pursuant to another aspect of the present invention, for treating post-transfusion purpura or neonatal alloimmune thrombocytopenia, comprising the step of administering to an individual a formulation comprised of a peptide in a pharmacologically effective concentration and a physiologically-compatible carrier therefor, where the individual (i) suffers from post-transfusion purpura or is the mother of a fetus at risk for developing NATP and (ii) has anti-$Bak^a$ or anti-$Bak^b$ antibodies, said peptide binding an antibody selected from the group consisting of an anti-$Bak^a$ antibody and an anti-$Bak^b$ antibody.

In accordance with yet another aspect of the present invention, an isolated DNA molecule has been provided that comprises a nucleotide sequence corresponding to a portion of the GPIIb gene that includes a nucleotide corresponding to nucleotide 2622 of GPIIb cDNA, wherein the molecule is not coincident with the GPIIb gene.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

(Bak$^b$ allele) for a guanine (G) (Bak$^a$ allele) at base 2622. (See below regarding the number of nucleotides herein.)

Figure 3:
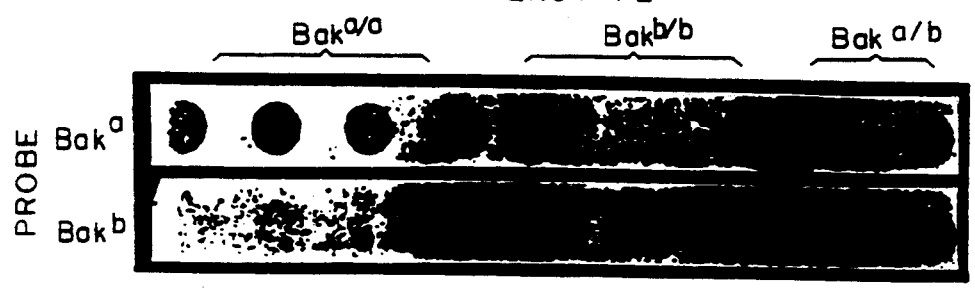

FIG. 3 shows an autoradiograph of the results of an analysis of Bak phenotype by allele-specific oligonucleotide hybridization. Bases 1988 to 2821 were enzymatically amplified from platelet RNA from nine individuals of known Bak phenotype. An allele-specific oligonucleotide (Probe A) hybridized to DNA from Bak$^a$ homozygous individuals (wells 1-4). A second allele-specific oligonucleotide (Probe B) hybridized to DNA from Bak$^b$ homozygous individuals (wells 5-7). Heterozygous individuals were positive with both probes (wells 8 and 9).

Figures 1, 4:
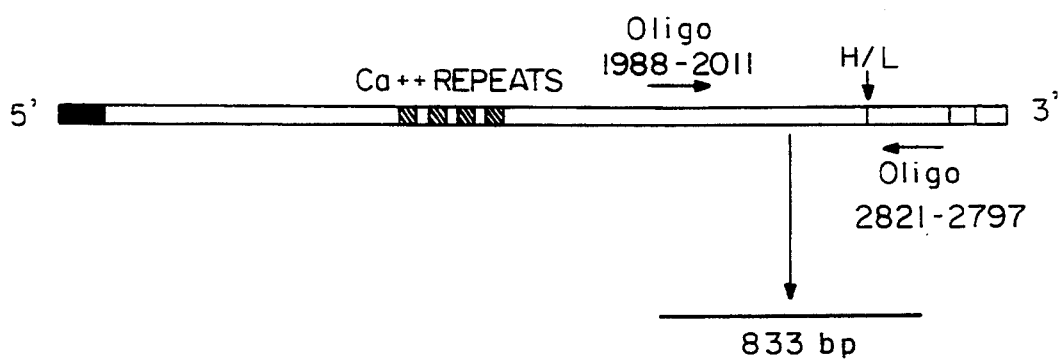
FIG. 1 is a diagrammatic representation of the GPIIb mRNA molecule. The locations of two oligonucleotide primers used for PcR amplification are also shown.

FIG. 4 is the amino acid sequence of the region of GPIIb responsible for the Bak polymorphism.

FIGS. 5A-5M present the prior art cDNA and corresponding amino acid sequences for the platelet membrane glycoprotein IIb as reported and numbered in Poncz et al., *J. Biol. Chem.* 262:8476 (1987).

DETAILED DESCRIPTION OF THE PREFERRED EMBODIMENTS

It has been discovered that a single nucleotide of GPIIb is responsible for the Bak polymorphism. In light of this discovery, manipulation of nucleic-acid molecules derived from platelets can be effected to provide for the analysis of alloantigen phenotypes, for the generation of peptides encoded by these molecules, and for the use of such peptides in diagnosis and therapy relating to a human platelet Bak polymorphism. Nucleic-acid molecules utilized in these contexts may be amplified, as described below, and generally include RNA, genomic DNA and cDNA derived from RNA.

Although the generation of cDNA from platelet or red blood cell mRNA was previously thought to be unfeasible, a new approach has been discovered for examining platelet mRNA from single individuals. As described in copending U.S. application Ser. No. 07/343,827, the contents of which are hereby incorporated by reference, is been found that mRNA can be obtained from platelets as well as red blood cells in quantities sufficient for isolation, cDNA generation, and amplification. By generating and amplifying cDNA produced from mRNA of a number of individuals of known platelet allotypes, the nucleotide sequence variations that exist in the genes that express alloantigen determinants can be ascertained. Furthermore, by isolating and amplifying mRNA from a number of individuals of known allotype, it is possible, pursuant to the present invention, to identify phenotype-specific nucleotide sequence variations in corresponding genes.

To obtain amplified cDNA from platelet mRNA, mRNA derived via conventional methods, see, e.g., MANIATIS, ET AL., MOLECULAR CLONING: A LABORATORY MANUAL 187-210 (Cold Spring Harbour Laboratory, 1982), from platelets can be converted to cDNA and then enzymatically amplified to produce microgram quantities of platelet-specific cDNA. This amplification is preferably accomplished via the "polymerase chain reaction" (PcR) method disclosed by U.S. Pat. Nos. 4,683,195 and 4,800,159, the respective contents of which are hereby incorporated by reference.

More specifically, in the process of generating and amplifying cDNA encoded by the isolated platelet mRNA, oligonucleotide primer pairs can be constructed that allow enzymatic amplification of a cDNA segment obtained from an mRNA molecule that encodes an amino-acid sequence defining the polymorphism. The corresponding, isolated cDNAs can then be analyzed to determine the molecular basis of observed phenotypic differences. The ability to compare directly the nucleotide and corresponding amino-acid sequences of genes encoding alleles of alloantigens is made possible by (1) the discovery that cDNA can be generated and amplified successfully from platelet mRNAs and (2) the determination of a nucleotide sequence of a glycoprotein which is thought to be polymorphic.

The molecular description of polymorphisms associated with platelet alloantigens can be provided by analyzing amplified cDNA, generated from platelet mRNA, according to one of the following methods: differential restriction endonuclease digestion (DRED), allele-specific oligonucleotide probing (ASOP), and ligase-mediated gene detection (LMGD). Additional methods of analysis would also be useful in this context, such as fluorescence resonance energy transfer (FRET) as disclosed by Wolf, et al., *Proc. Nat. Acad. Sci. USA* 85: 8790-94 (1988), the contents of which are hereby incorporated by reference.

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet mRNA is digested and the resulting fragments are analyzed by size. The presence or absence of nucleotide fragments, corresponding to the endonuclease-cleaved fragments, determines which phenotype is present.

Thus, a guanine(G) thymine(T) polymorphism at base 2622 is revealed by examination of the nucleotide sequence contained in cDNA generated from mRNA derived from Bak$^b$-homozygous vs. Bak$^a$-homozygous individuals. (Throughout this description, the numbering of nucleotides in mRNAs and cDNAs is with reference to the cDNA sequence disclosed by Poncz, et al., *J. Biol. Chem.* 262:8476 (1987), the contents of which article are hereby incorporated by reference. See FIGS. 5A-5M. A nucleotide of genomic DNA that corresponds to a particular nucleotide in a cDNA is designated by the number of the cDNA nucleotide.) This single nucleotide substitution results in the creation of a unique restriction enzyme cleavage site for the restriction endonuclease FokI. By utilizing a restriction endonuclease with the selectivity of FokI or an isoschizimer thereof to discriminate between these two polymorphic sequences, the phenotypes of individuals can be determined in the above-described manner. Sequence analysis of the resulting restriction fragments demonstrates that the Bak$^b$ form of GPIIb mRNA contains the codon AGC, encoding serine at position 843 of the known GPIIb amino-acid sequence, in place of an ATC codon coding for isoleucine at position 843 in the Bak$^a$ form. (The designation of amino acid residues in this regard follows the numbering system of Poncz, et al., incorporated above by reference. See FIGS. 5A-5M.)

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a platelet membrane glycoprotein. Such a probe would be discernably labeled so that when it hybridizes to the allele-distinguishing cDNA segment, it can be detected and the specific allele thus identified.

For example, an oligonucleotide probe can be synthesized, in accordance with the present invention, that will hybridize to a cDNA segment, derived from GPIIb mRNA, that contains the base thymine at polymorphic nucleotide 2622 (nucleotide=thymidylate). Alternatively, an oligonucleotide probe of the present invention will hybridize what the cDNA segment contains the base guanine at nucleotide 2622 (nucleotide=guanylate). These allele-specific probes can be appropriately labeled and added to the generated cDNA segments under annealing conditions, such that one of the allele-specific probes hybridizes and can be detected, thereby identifying the specific BAk$^a$ or Bak$^b$ allele. In accordance with conventional procedure, the design of an oligonucleotide probe according to the present invention preferably involves adjusting probe length to accommodate hybridization conditions (temperature, ionic strength, exposure time) while assuring allele-specificity. A length of ten to thirty nucleotides is typical.

In the course of the third method of analysis, LMGD, as disclosed by Landegren, et al., *Science* 241:1077-80 (1988), the contents of which are hereby incorporated by reference, a pair of oligonucleotide probes are synthesized that will hybridize adjacently to each other, i.e., to a cDNA segment under appropriate annealing conditions, at the specific nucleotide that distinguishes one allele from other alleles of a platelet membrane glycoprotein. Each of the pair of specific probes is labeled in a different manner, and, when both probes hybridize to the allele-distinguishing cDNA segment, the probes can be ligated together by the addition of a ligase.

When the ligated probes are separated and isolated from the cDNA segments, both types of labeling can be observed together on a Northern blot when analyzed by conventional procedures, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments, each type of labeling is observed to be separate from the other label type.

An exemplary LMGD analysis, according to the present invention, entails the use of a pair of oligonucleotide probes, wherein one probe is radioactively $^{32}$p-labeled and the other probe is biotin-labeled. Under appropriate conditions, the pair of probes adjacently hybridizes to a cDNA segment at a nucleotide corresponding to nucleotide 2622 of GPIIb. The biotin labeled probe hybridizes to nucleotides 2602-2622 of GPIIb, wherein nucleotide 2622 contains a thymine, which distinguishes the Bak$^b$ allele. The $^{32}$p-labeled probe hybridizes nucleotides 2623-2633 of GPIIb and, therefore will hybridize adjacently to the biotin-labeled probe. These probes are then added under annealing conditions such that they hybridize adjacently to each other spanning nucleotides 2602-2633 of GPIIb. The biotin labeled probe is detected by the binding of the compound strepavidin after hybridization and the p$^{32}$- labeled probe is detected by autoradiography, according to conventional procedures.

When the Bak$^b$ allele sequence is present in the amplified cDNA, then the addition of a ligase will result in the biotin labeled probe being covalently bound to the $^{32}$p-labeled probe. The ligation is possible, because the ends of the probes that are adjacent to each other (hybridized to nucleotides (2622 and 2633) are both hybridized to the cDNA. In the case where these two probes hybridize to the Bak$^b$ allelic form of the cDNA sequence, the biotin-labeled probe end at nucleotide 2622 is not hybridized appropriately, preventing the ligation step from occurring. When this pair of probes binds completely to the Bak$^b$ allele sequence, therefore, the probes are ligated and when the probes are separated from the Bak$^b$ sequence and exposed so as to be detected, both the biotin/strepavidin and the $^{32}$p labeling are present together. When the Bak$^a$ allele sequence is hybridized, on the other hand, the probes cannot be ligated, and the biotin/strepavidin- and $^{32}$p-labeling are observed separately. In this manner, the Bak$^b$ and Bak$^a$ alleles sequences and corresponding phenotype can be distinguished.

Alternatively, DRED, ASOP and LMGD or other suitable methods of analysis, such as FRET, can be used with genomic or amplified-genomic DNA to distinguish platelet membrane glycoprotein Bak$^b$ from Bak$^a$, starting with any nucleated cell sample, obtained from an individual, from which DNA can be isolated in sufficient quantities for analysis. Amplified genomic DNA would be amplified from isolated genomic DNA in the same manner as described above for cDNA. Once a tissue sample, such as cells scraped from the inside of an individual's cheek, has been obtained, genomic DNA isolated by conventional procedures can be analyzed directly per se or amplified prior to analysis.

The foregoing description of the three types of analysis would apply to the use of genomic DNA or amplified-genomic DNA, with the term "cDNA" being replaced with "genomic or amplified genomic DNA." One difference in the analysis of genomic DNA or amplified genomic DNA is that the GPIIb sequence used for designing a suitable oligonucleotide probe might have to include any intronic sequences, which would not be present in the cDNA of GPIIb, that were near or adjacent to the nucleotide that determines the Bak phenotype.

In general, the presence of intronic sequences near the phenotype-determining nucleotide can be ascertained by sequence analysis of genomic DNA, accomplished via Maxam-Gilbert or another conventional technique. Sequence information on the region of genomic DNA encompassing an exon that encodes the polymorphism can be used to design appropriate oligonucleotides, such that a genomic DNA-based PcR could be performed. The resulting amplified products can then be assessed for alloantigen phenotype, in accordance with the present invention, by means of any of the above-described diagnostic methods.

The polymorphic nucleotide which distinguishes the above-described GPIIb alleles is located (see asterisk) in an exon shown below with flanking genomic segments. In accordance with convention, the following is the coding sequence of the genomic DNA; the GPIIb amino-acid residues encoded by the exon are also shown, with conventional acronyms used (v for valine, d for aspartic acid, etc.):

```
...CTCAAGGTAAGAGCTGGGTGGAAGAAAGACCTGGGAAGGCGGCCCCA
   ----------------
   (end of    (intron>
   an exon)

GACCAACCACCGGGGCACCTCTGTGGGCTGGGGTT

CGGGGGAGACCTGGGCCTGACCACTCCTTTGCCCCCCCAGGTGGACTGGGGG
                                      v  d  w  g
              (exon starts at underscored "AG")

CTGCCCATCCCCAGCCCCTCCCCCATTCACCCGGCCCATCACAAGCGGGAT
 l  p  i  p  s  p  s  p  i  h  p  a  h  h  k  r  d
    *
```

```
CGCAGACAGATCTTCCTGCCAGAGCCCGAGCAGCCCTCGAGGCTTCAGGAT
 r  r  q  i  f  l  p  e  p  e  q  p  s  r  l  q  d

CCAGTTCTCGTAGTGAGCAGGCTCTCTGGTCTCGGGCCCGGCCTCCC
 p  v  l  v
              (exon ends at underscored "GT")

CGGGACCCACGGGGCAGAGGGGATGGGAGGAGGGAG...
```

(Sequence data provided by Dr. Mortimer Poncz, The Children's Hospital of Philadelphia.) More generally, the primers used for PcR amplification should be positioned, relative to the exon which contains the polymorphic nucleotide, so that the amplified region encompasses that nucleotide, which corresponds to base 2622 of the GPIIb cDNA. For example, the solid bar and striped bar above denote, respectively, a sequence of a first primer and the complementary sequence of a second primer which are suitable for genomic amplification as described herein.

The ability to perform DNA-typing analysis for determination of Bak phenotypes, pursuant to the present invention, has a number of useful clinical applications, including but not limited to those involving determination of the Bak alloantigen phenotype of an individual, and the diagnosis and treatment of a pathological immune response (or potential response) involving foreign alloantigens or antibodies. In accordance with the present invention, alloantigen phenotyping can be effected by the generation of amplified genomic DNA or amplified cDNA from platelet mRNA, permitting diagnosis of individuals for the purpose of treating or preventing pathological immune responses.

Once the nucleotide-sequence variations specific for each allelic form of the alloantigens of a given class are determined, other conventional methods can be employed, through the use of genomic DNA or platelet RNA, to perform the same type of diagnosis on other individuals. These methods would include, but not are limited to, allele-specific nucleotide probing and ligase-mediated gene detection, as previously described.

Diagnostic kits can also be used, in accordance with the present invention, for the determination and diagnosis of alloantigen phenotypes via the procedures described herein. Such a kit can include, inter alia, antibodies or antibody fragments to an antigenic determinant expressed by either of the above-described Bak$^a$- and Bak$^b$-encoding sequences, which antibodies would react with the blood sample of an individual so as to indicate whether that individual has a Bak$^a$ or Bak$^b$ phenotype. Alternatively, all the reagents required for the detection of nucleotide(s) that distinguish the Bak alloantigens, by means described herein, can be provided in a single kit that uses isolated genomic DNA or platelet mRNA from an individual. Containing a labeled probe that distinguishes, for example, nucleotide 2622 of GPIIb, such a kit can be utilized for Bak alloantigen phenotyping.

A further beneficial use of the nucleotide sequences that distinguish the Bak$^a$ allele from the Bak$^b$ allele is to obtain or synthesize the respective expression product, in the form of a polypeptide, encoded by these nucleotide sequences. These polypeptides can be used to generate antibodies for diagnostic and therapeutic uses, for example, with regard to pathological conditions such as PTP or NATP.

A polypeptide within the present invention which can be used for the purpose of generating such antibodies preferably comprises an amino-acid sequence that corresponds to (i.e., is coincident with or functionally equivalent to) a four-residue (tetramer) fragment of the GPIIb molecule that includes amino acid 843. When the latter amino acid is serine, the polypeptide can be used, as described above, to produce antibodies that specifically bind the Bak$^b$ form of GPIIb; when it is isoleucine, antibodies can be obtained that particularly recognize the Bak$^a$ form. The class of polypeptides thus defined, in accordance with the present invention, is not intended to include the GPIIb molecule itself, but does encompass fragments of the molecule as well as synthetic polypeptides meeting the aforementioned definition.

Although the length of a polypeptide within this class is not critical, the requirement for immunogenicity may require that the polypeptide be attached to a immunogenicity-imparting carrier, e.g., a particulate carrier like a liposome or a soluble macromolecule (protein or polysaccharide) with a molecular weight in the range of about 10,000 to 1,000,000, or be administered with an adjuvant, such as complete Freund's adjuvant. For artificial polypeptides, as distinguished from GPIIb fragments, maximum length is determined largely by the limits of techniques available for peptide synthesis, say, about fifty amino acids. Thus, a synthetic polypeptide of the present invention is preferably between four and about fifty amino acids in length.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of antibodies the bind preferentially to either the Bak$^a$ form or the Bak$^b$ form of GPIIb. "Antibody" also encompasses fragments, like Fab and F(ab')$_2$, of anti-Bak$^a$ or anti-Bak$^b$ antibodies, and conjugates of such fragments, and so-called "antigen binding proteins" (single-chain antibodies) which are based on anti-Bak$^a$ or anti-Bak$^b$ antibodies, in accordance, for example, with U.S. Pat. No. 4,704,692, the contents of which are hereby incorporated by reference. Human alloantisera currently used for serological typing are specifically excluded from this definition. Alternatively, Mabs or a fragment thereof within the present invention can be produced using conventional procedures via the expression of isolated DNA which codes for variable regions of such an Mab in host cells like E. coli, see, e.g., Ward, et al., Nature, 341:544–546 (1989), or transfected murine myeloma cells. See Gillies, et al., Biotechnol. 7: 799–804 (1989); Nakatani, et al., Biotechnol. 7:805–10 (1989).

Diagnostic applications of these antibodies are exemplified, according to the present invention, by the use of a kit containing an anti-Bak$^a$ or an anti-Bak$^b$ antibody which undergoes a reaction with a sample of an individual's blood to determine a Bak$^a$ or Bak$^b$ platelet phenotype. Such a reaction involves the binding of anti-Bak$^a$ antibody to Bak$^a$ antigen or the binding of anti-Bak$^b$ antibody to Bak$^b$ antigen. The observation antibody-antigen complex in a blood sample would indicate a positive result. A kit of this sort could be used to diagnose, or to help prevent, the occurrence of pathological conditions like PTP or NATP.

A polypeptide of the present invention that is recognized specifically by anti-Bak$^a$ or anti-Bak$^b$ antibodies can be used therapeutically. Thus, antibodies raised against such a polypeptide can employed in the generation, via conventional methods, of anti-idiotypic antibodies (that is, antibodies that bind an anti-Bak$^a$ or anti-Bak$^b$ antibody), e.g., by the use of hybridomas as described above. See, for example, U.S. Pat. No. 4,699,880, the contents of which are hereby incorporated by reference. Such anti-idiotypic antibodies would bind endogenous or foreign anti-Bak antibodies in the blood of an individual, thereby to treat or prevent pathological conditions associated with an immune response to a "foreign" Bak alloantigen. Alternatively, a polypeptide within the present invention can be administered, with a physiologically-compatible carrier, to achieve the same qualitative effect, namely, the selective reduction or elimination of circulating anti-Bak antibodies from a patient suffering or at risk from an immune response.

The present invention is further described below by reference to the following, illustrative examples. Used in the examples were platelet samples from four homozygous Bak$^a$ individuals, three homozygous Bak$^b$ individuals, and two individuals who were heterozygous for the Bak allotype. The respective phenotypes of all the test subjects had been identified using well-characterized anti-Bak$^a$ and anti-Bak$^b$ human alloantisera.

EXAMPLE 1: AMPLIFICATION OF cDNA

Platelet RNA from a panel of nine normal volunteers, including four Bak$^{a/a}$, three Bak$^{b/b}$ and two Bak a/b individuals, was prepared according to the procedure developed by Chomczynski and Sacchi, Anal. Biochem. 162:156 (1987), except that the final RNA pellet was subjected to one additional phenol/chloroform extraction and ethanol precipitation necessary to achieve reproducible gene amplification of platelet cDNA. Bak$^a$ and Bak$^b$ phenotype was assessed using well-characterized human alloantisera in a standard antigen capture assay, see Furihata, et al., J. Clin. Invest. 80:1624 (1987); Chomczynski and Sacchi, Anal. Biochem. 162:156 (1987). The C-terminal end of the GPIIb heavy and light chain message from base 1988 to 2821 was selected for sequence analysis and comparison, and two 24-base oligonucleotide primers flanking 833 base pairs of this region were synthesized on a Gene Assembler (Pharmacia Fine Chemicals, Piscataway, N.J.).

The anti-sense primer (5'-CAGGAAGGCCAG-CACCGTGACCATG-3') from base 2821 to 2797 was used to prime the synthesis of cDNA from platelet RNA as previously described (Newman, et al., J. Clin. Invest. 82:739 (1988); Newman, et al., J. Clin. Invest. 83:1778 (1989). The second strand was generated by the sense primer (5'GAGCTGCAGATGGACGCAGC-CAAC-3') from base 1988 to 2011 during the first round of PcR. Amplification was carried out in a DNA Thermal Cycler (Perkin-Elmer Cetus, Norwalk, Conn.) programmed to permit denaturation at 94° C. for on ½-minute, annealing at 50° C. for one ½-minute, and chain extension at 72° C. for three minutes. The reaction was allowed to proceed for 30 cycles followed by a final incubation at 72° C. for seven minutes to allow completion of strand synthesis.

EXAMPLE 2: ANALYSIS OF PcR PRODUCTS

PcR samples were analyzed on 1.8% Seakem GTG agarose gels (FMC BioProducts, Rockland, Me.), and the appropriate bands were excised and recovered by electroelution. The plasmid vector pGEM-5Zf (Promega Biotech, Madison, Wis.) was prepared for ligation by restriction digestion with Eco RV (New England Biolabs, Beverly, Mass.) to yield blunt ends, and ligated to purified amplification product, followed by transformation into E. coli strain NM522 competent cells (Stratagene Cloning Systems, San Diego, Calif.). Two clones representing each Bak homozygous phenotype were selected for direct sequence analysis of the plasmid DNA by the dideoxy sequencing method using T7 DNA polymerase (USB, Cleveland, Ohio USA). Four 24 or 25 base oligonucleotides were synthesized and used as sequencing primers.

Figure 2:
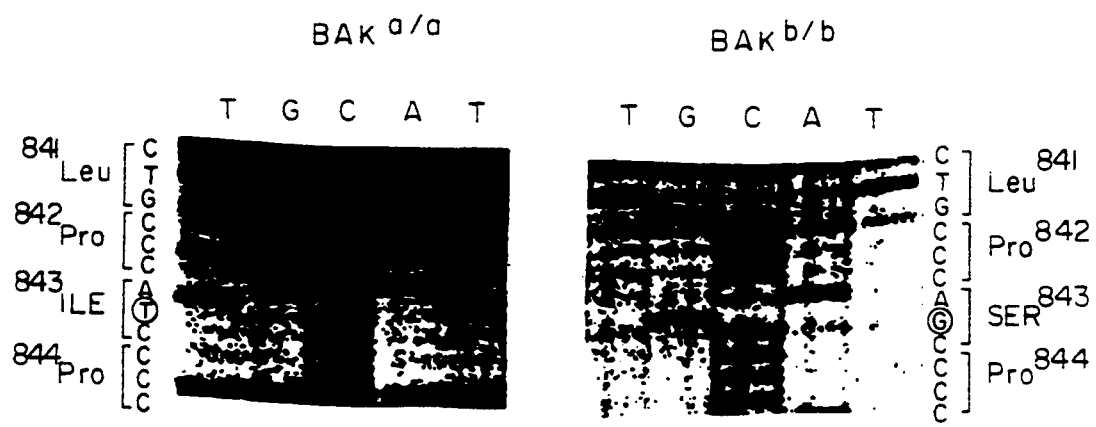
FIG. 2 shows autoradiographs of electrophoretic gels used in the sequence analysis of amplified GPIIb cDNA, derived from both a $Bak^a$ homozygous individual and a $Bak^b$ homozygous individual. A segment of the autoradiograph, encompassing bases 2615 to 2626 indicates a single base substitution of a thymine (T)

The results (shown in FIG. 2) demonstrated that a single nucleotide difference was observed between the Bak$^{a/a}$ and Bak$^{b/b}$ clones at base 2622. Analysis of the cDNA derived from the Bak$^{a/a}$ individual revealed that thymine was present at this position, whereas guanine was substituted in this position in the Bak$^{b/b}$ cDNA. This resulted in a substitution of a serine for an isoleucine at amino acid residue 843.

EXAMPLE 3: ALLELE-SPECIFIC HYBRIDIZATION

Amplified cDNA from four individuals with Bak$^{a/a}$ phenotype, three with Bak$^{b/b}$, and two heterozygous for Bak was subjected to hybridization with 13-base allele-specific oligonucleotides (ASO). Probe A (TGCCCATCCCCAG) corresponds to the published sequence of GPIIb (Poncz, et al., *J. Biol. Chem.* 262(18):8476 (1987)) from base 2616 to 2628, while Probe B (TGCCCAGCCCCAG) differs only in the middle base, a G instead of a T, and corresponds to a single base difference observed in the region sequenced. The probes (200 ng) were end-labeled with digoxigenin-11-dUTP (Boehringer Mannheim, Indianapolis, Ind.) in 25 μl 100 mmol/L potassium cacodylate, 2 mmol/L CoCl$_2$, 0.2 mmol/L DTT, pH 7.2 containing 1 U terminal transferase (Boehringer Mannheim, Indianapolis, Ind.), and the probes were used for hybridization without purification. Amplified DNA was used directly for blotting or, in some cases, appropriate bands were recovered from agarose gels using Gene Clean (Bio 101, LaJolla, Calif.). The samples were eluted in 20 μl water, diluted 1/10,000, and 10 μl was used for reamplification using the same probes and PcR conditions. Amplified or reamplified DNA was denatured in 0.25 N NaOH, 1.5 mol/L NaCl at room temperature for 15 minutes. Each sample was divided between two wells of a Minifold dot blot apparatus (Schleicher and Schuell, Keene, N.H.) and transferred to Magnagraph nylon membrane (MSI, Westboro, Mass.) by vacuum suction. The filter was exposed to UV irradiation (Fotodyne, New Berlin, Wis.) for 5 minutes followed by baking at 80° C. for 15 minutes. The membrane was prehybridized in 5X Denhardt's, 5X SSC, 10 mmol/L EDTA, 10 mmol/L Na$_2$HPO$_4$, pH 7 at 68° C. for one hour, and then cut into two strips which were hybridized to either Probe A or Probe B in 4 mls 10X Denhardt's 5X SSC, 5 mmol/L EDTA, 7% SDS, 50 ug/ml Salmon sperm DNA, 20 mmol/l Na$_2$HPO$_4$, pH 7 at 42° C. overnight. The filters were washed in 2 changes 6X SSC for 30 minutes each at room temperature followed by 2 changes of 3 mol/L tetramethylammonium chloride (Aldrich Chemical, Milwaukee, Wis.), 2 mmol/L EDTA, 1% SDS, 50 mmol/L Tris, pH 8 for 20 minutes each at 42° C. Positive hybridizations using The Genius kit (Boehringer Mannheim, Indianapolis, Ind.) which employs an alkaline phosphatase-conjugated antidigoxigenin antibody, according to the manufacturer's directions.

The results, shown in FIG. 3, demonstrated that Probe A was positive with the four Bak$^{a/a}$ homozygous individuals, Probe B was positive with the three Bak$^{b/b}$ homozygous individuals, and both probes were positive with amplified DNA from the two heterozygous individuals analyzed.

What is claimed is:

1. A kit for typing platelet Bak alloantigens, comprising (a) means for amplifying at least a portion of a GPIIb gene, wherein the amplified portion includes the nucleotide corresponding to nucleotide 2622 of the corresponding GPIIb cDNA, and wherein said portion is of sufficient length for identification of said nucleotide corresponding to nucleotide 2622 of the corresponding GPIIb cDNA by hybridization with a labeled oligonucleotide probe or by restriction endonuclease digestion; and (b) at least one component selected from the group consisting of (i) a receptacle containing a solution of a labeled oligonucleotide probe that distinguishes a Bak$^a$-allele nucleotide sequence from a Bak$^b$-allele nucleotide sequence, said sequences comprising a nucleotide of genomic DNA corresponding to nucleotide 2622 of a GPIIb cDNA and (ii) a receptacle containing a solution of a restriction endonuclease which recognizes a cleavage site that distinguishes a Bak$^a$-allele nucleotide sequence from a Bak$^b$-allele nucleotide sequence, said sequences comprising a nucleotide of genomic DNA corresponding to nucleotide 2622 of a GPIIb cDNA.

2. A kit for typing platelet Bak alloantigens, comprising (a) means for amplifying at least a portion of a GPIIb cDNA, wherein the amplified portion includes nucleotide 2622 of the GPIIb cDNA and wherein said portion is of sufficient length for identification of nucleotide 2622 of the cDNA by hybridization with a labeled oligonucleotide probe or by restriction endonuclease digestion; and (b) at least one component selected from the group consisting of (i) a receptacle containing a solution of a labeled oligonucleotide probe that distinguishes a Bak$^a$-allele nucleotide sequence from a Bak$^b$-allele nucleotide sequence, said sequences comprising the nucleotide at position 2622 of a GPIIb cDNA; and (ii) a receptacle containing a solution of a restriction endonuclease which recognizes a cleavage site that distinguishes a Bak$^a$-allele nucleotide sequence from a Bak$^b$-allele nucleotide sequence, said sequences comprising the nucleotide at position 2622 of a GPIIb cDNA.

3. A method of typing glycoprotein GPIIb comprising the steps of (A) synthesizing cDNA from mRNA from human platelets of a first individual; (B) amplifying a portion of the cDNA synthesized in step (A) that encodes at least part of glycoprotein GPIIb, said amplified portion containing nucleotide 2622 of the GPIIb cDNA; and (C) analyzing amplified cDNA from step (B) by a method which distinguishes a Bak$^a$-allele nucleotide sequence from a Bak$^b$-allele nucleotide sequence, said sequences comprising the nucleotide at position 2622 of a GPIIb cDNA, in order to determine the Bak allele or alleles carried by said first individual.

4. A method as claimed in claim 3 further comprising the step of synthesizing cDNA from human platelet mRNA of a second individual, repeating steps (B) and (C) on the cDNA of said second individual, and thereafter discriminating between said first and second individuals based on the Bak alleles carried by them, respectively.

5. A method as claimed in claim 3 wherein step (C) comprises the steps of (i) preparing cDNA fragments by digesting said amplified cDNA with a restriction endonuclease which recognizes a cleavage site that distinguishes a Bak$^a$-allele nucleotide sequence from a Bak$^b$-allele nucleotide sequence, said sequences comprising the nucleotide at position 2622 of a GPIIb cDNA, and (ii) analyzing said cDNA fragments to determine said Bak allele or alleles.

6. A method as claimed in claim 3 wherein step (C) comprises the steps of (i) hybridizing said amplified cDNA with a labeled allele-specific oligonucleotide probe that distinguishes a Bak$^a$-allele nucleotide sequence from a Bak$^b$-allele nucleotide sequence, said sequences comprising the nucleotide at position 2622 of a GPIIb cDNA, and then (ii) analyzing the Bak-allele specificity of said probe that has hybridized to said amplified cDNA to determine said Bak allele or alleles.

7. A method as claimed in claim 3, wherein step (C) comprises the steps of (i) hybridizing said amplified cDNA with a pair of oligonucleotide probes to produce a construct, wherein the first probe of said pair is labeled with a first label and the second probe of said pair is labeled with a second label, such that the first label is distinguishable from the second label, and the probes hybridize adjacently to each other at the nucleotide of the amplified cDNA that corresponds to a nucleotide at position 2622 of a GPIIb cDNA; and thereafter (ii) reacting said construct with a ligase in a reaction medium; and then (iii) analyzing said reaction medium to detect the presence of a ligation product comprising said first probe ligated to said second probe.

8. A method of typing platelet Bak membrane glycoprotein GPIIb comprising the steps of (A) obtaining from a first human individual genomic DNA which comprises a nucleotide corresponding to nucleotide 2622 of a GPIIb cDNA and (B) analyzing said genomic DNA by a method which distinguishes a $Bak^a$-allele nucleotide sequence from a $Bak^b$-allele nucleotide sequence, said sequences comprising a nucleotide of genomic DNA corresponding to the nucleotide at position 2622 of a GPIIb cDNA, in order to determine the Bak allele or alleles carried by said first individual.

9. A method as claimed in claim 8 further comprising the step of obtaining from a second human individual genomic DNA which comprises a nucleotide corresponding to nucleotide 2622 of a GPIIb cDNA, repeating step (B) on the genomic DNA of said second individual, and thereafter discriminating between said first and second individuals based on the Bak alleles carried by them, respectively.

10. A method as claimed in claim 8 wherein step (B) comprises the steps of (i) preparing genomic DNA fragments by digesting said genomic DNA, which comprises a nucleotide corresponding to nucleotide 2622 of a GPIIb cDNA, with a restriction endonuclease which recognizes a cleavage site that distinguishes a $Bak^a$-allele nucleotide sequence from a $Bak^b$-allele nucleotide sequence, said sequences comprising a nucleotide which corresponds to the nucleotide at position 2622 of a GPIIb cDNA, and (ii) analyzing said genomic DNA fragments with a labeled probe to determine said Bak allele or alleles.

11. A method as claimed in claim 8 wherein step (B) comprises the steps of (i) preparing genomic DNA fragments by digesting said genomic DNA with a restriction endonuclease, provided that said DNA fragments which comprise the nucleotide corresponding to nucleotide 2622 of a GPIIb cDNA are of sufficient length for identification of said nucleotide corresponding to nucleotide 2622 of a GPIIb cDNA by hybridization with a labeled oligonucleotide probe, (ii) hybridizing said DNA fragments with a labeled allele-specific oligonucleotide probe that distinguishes a $Bak^a$-allele nucleotide sequence from a $Bak^b$ allele nucleotide sequence, said sequences comprising a nucleotide corresponding to the nucleotide at position 2622 of a GPIIb cDNA, and (iii) analyzing the Bak-allele specificity of said probe that has hybridized to said DNA fragments to determine said Bak allele or alleles.

12. A method as claimed in claim 8, wherein step (B) comprises the steps of (i) hybridizing said genomic DNA with a pair of oligonucleotide probes to produce a construct, wherein the first probe of said pair is labeled with a first label and the second probe of said pair is labeled with a second label, such that the first label is distinguishable from the second label, and the probes hybridize adjacently to each other at the nucleotide of the genomic DNA that corresponds to a nucleotide at position 2622 of a GPIIb cDNA; and thereafter (ii) reacting said construct with a ligase in a reaction medium; and then (iii) analyzing said reaction medium to detect the presence of a ligation product comprising said first probe ligated to said second probe.

13. A method of typing platelets to identify a Bak alloantigen phenotype, comprising the steps of (A) obtaining genomic DNA from a first human individual; (B) amplifying a portion of the genomic DNA obtained in step (A) that is at least part of the genomic DNA for glycoprotein GPIIb, said amplified portion containing the nucleotide of genomic DNA corresponding to nucleotide 2622 of the GPIIb cDNA; and (C) analyzing amplified DNA from step (B) by a method which distinguishes a $Bak^a$-allele nucleotide sequence from a $Bak^b$-allele nucleotide sequence, said sequences comprising a nucleotide corresponding to the nucleotide at position 2622 of a GPIIb cDNA, in order to determine the Bak allele or alleles carried by said first individual.

14. A method as claimed in claim 13 further comprising the step of obtaining genomic DNA from a second human individual, repeating steps (B) and (C) on the genomic DNA of said second individual, and thereafter discriminating between said first and second individuals based on the Bak alleles carried by them, respectively.

15. A method as claimed in claim 13 wherein step (C) comprises the steps of (i) digesting said amplified portion of genomic DNA with a restriction endonuclease to produce DNA fragments, said restriction endonuclease recognizing a cleavage site in said amplified portion that distinguishes a $Bak^a$-allele nucleotide sequence from a $Bak^b$-allele nucleotide sequence, said sequences comprising a nucleotide corresponding to the nucleotide at position 2622 of a GPIIb cDNA, and (ii) analyzing said DNA fragments to determine said Bak allele or alleles.

16. A method as claimed in claim 13 wherein step (C) comprises (i) hybridizing said amplified portion of genomic DNA with a labeled allele-specific oligonucleotide probe that distinguishes a $Bak^a$-allele nucleotide sequence from a $Bak^b$ allele nucleotide sequence, said sequences comprising a nucleotide corresponding to the nucleotide at position 2622 of a GPIIb cDNA, and then (ii) analyzing the Bak-allele specificity of said probe that has hybridized to said amplified portion of genomic DNA to determine said Bak allele or alleles.

17. A method as claimed in claim 13 wherein step (C) comprises the steps of (i) hybridizing said amplified portion of genomic DNA with a pair of oligonucleotide probes to produce a construct, wherein the first probe of said pair is labeled with a first label and the second probe of said pair is labeled with a second label, such that the first label is distinguishable from the second label, and the probes hybridize adjacently to each other at the nucleotide of the amplified portion of the genomic DNA that corresponds to a nucleotide at position 2622 of a GPIIb cDNA; and thereafter (ii) reacting said construct with a ligase in a reaction medium; and then (iii) analyzing said reaction medium to detect the presence of a ligation product comprising said first probe ligated to said second probe.

* * * * *

UNITED STATES PATENT AND TRADEMARK OFFICE
CERTIFICATE OF CORRECTION

PATENT NO.   : 5,436,163
DATED        : July 25, 1995
INVENTOR(S)  : Peter J. Newman, et al.

It is certified that error appears in the above-indentified patent and that said Letters Patent is hereby corrected as shown below:

In column 6, line 37          -- <----> -- should
be added after "guanine(G)".

In column 9, lines 1-25          the sequence
diagram should be as follows.

Signed and Sealed this

Sixth Day of August, 1996

BRUCE LEHMAN

Attest:

Attesting Officer        Commissioner of Patents and Trademarks

UNITED STATES PATENT AND TRADEMARK OFFICE
CERTIFICATE OF CORRECTION

PATENT NO.    : 5,436,163                                    Page 2 of 2
DATED         : July 25, 1995
INVENTOR(S)   : Peter J. Newman, et al.

It is certified that error appears in the above-indentified patent and that said Letters Patent is hereby corrected as shown below:

```
                                        →
...CTCAAGGTAAGAGCTGGGTGGAAGAAAGACCTGGGAAGGCGGCCCCA
   ----------
   (end of    (intron>
   an exon)

GACCAACCACCGGGGCACCTCTGTGGGCTGGGGTT

CGGGGGAGACCTGGGCCTGACCACTCCTTTGCCCCCCCAGGTGGACTGGGGG
                                            v  d  w  g
         (exon starts at underscored "AG")

CTGCCCATCCCCAGCCCCTCCCCCATTCACCCGGCCCATCACAAGCGGGAT
  l  p  i  p  s  p  s  p  i  h  p  a  h  h  k  r  d
        *

←
CGCAGACAGATCTTCCTGCCAGAGCCCGAGCAGCCCTCGAGGCTTCAGGAT
  r  r  q  i  f  l  p  e  p  e  q  p  s  r  l  q  d

CCAGTTCTCGTAGTGAGCAGGCTCTCTGGTCTCGGGCCCGGCCTCCC
  p  v  l  v
          (exon ends at underscored "GT")

CGGGACCCACGGGGCAGAGGGGATGGGAGGAGGGAG...
```